(12) United States Patent
Qiu

(10) Patent No.: US 8,389,657 B2
(45) Date of Patent: Mar. 5, 2013

(54) POLY(METH)ACRYLAMIDES AND POLY(METH)ACRYLATES CONTAINING FLOURINATED AMIDE

(75) Inventor: Weiming Qiu, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/446,537

(22) Filed: Apr. 13, 2012

(65) Prior Publication Data

US 2012/0264972 A1 Oct. 18, 2012

Related U.S. Application Data

(62) Division of application No. 12/787,651, filed on May 26, 2010, now Pat. No. 8,178,638, which is a division of application No. 11/500,532, filed on Aug. 8, 2006, now Pat. No. 7,754,838.

(51) Int. Cl.
C07C 229/00 (2006.01)

(52) U.S. Cl. .................. 526/248; 562/561; 562/564

(58) Field of Classification Search .................. 526/248; 562/561, 564
See application file for complete search history.

(56) References Cited

U.S. PATENT DOCUMENTS

| 2,782,184 A | 2/1957 | Husted et al. |
| 3,420,697 A | 1/1969 | Sweeney et al. |
| 3,446,570 A | 5/1969 | Sweeney et al. |
| 3,539,566 A | 11/1970 | Sweeney et al. |
| 3,553,179 A | 1/1971 | Bartlett |
| 3,576,017 A | 4/1971 | Sweeney et al. |
| 3,576,018 A * | 4/1971 | Sweeney et al. ............... 554/57 |
| 3,595,886 A | 7/1971 | Sweeney et al. |
| 3,651,069 A | 3/1972 | Sweeney et al. |
| 3,844,999 A | 10/1974 | Petrella |
| 6,054,615 A | 4/2000 | Qiu |
| 6,376,705 B1 | 4/2002 | Qiu |
| 6,689,854 B2 | 2/2004 | Fan et al. |
| 7,094,829 B2 * | 8/2006 | Audenaert et al. ............ 524/544 |

FOREIGN PATENT DOCUMENTS

| BE | 744474 | 8/1993 |
| DE | 1929554 | 2/1970 |
| EP | 0161804 A1 | 11/1985 |
| EP | 0457610 A2 | 11/1991 |
| JP | 63292520 | 11/1988 |
| JP | 03030825 | 2/1991 |
| JP | 04257373 | 9/1992 |
| WO | WO 2005/090420 A1 | 9/2005 |
| WO | WO 2006/061334 A1 | 6/2006 |

OTHER PUBLICATIONS

Koji Honda et al., "Molecular Aggregation Structure and Surface Properties of poly(fluoroalkylacrylate) Thin Films" Macromolecules (2005), 38(13), 5699-5705.

* cited by examiner

Primary Examiner — Ling Choi
Assistant Examiner — Chun-Cheng Wang

(57) ABSTRACT

A composition comprising a copolymer having repeating units in any sequence of Formula I

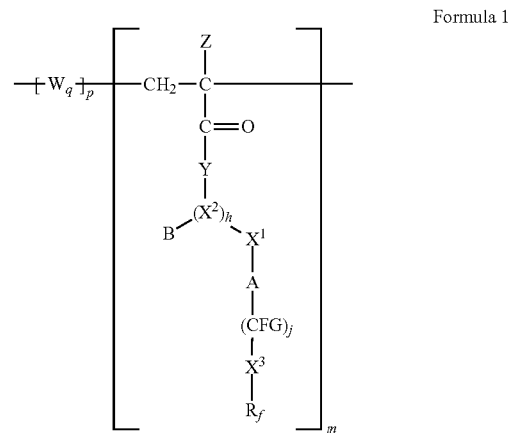

Formula 1 wherein
$R_f$ is a straight or branched perfluoroalkyl group which is optionally interrupted by at least one oxygen atom,
$X^3$ is oxygen or $X^1$,
each $X^1$ is independently an organic divalent linking group,
G is F or $CF_3$,
A is an amide,
$X^2$ is an organic linking group,
Y is O, N or S,
Z is H, a straight or branched alkyl group or halide,
B is H or

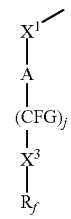

wherein
$R_f$, $X^1$, $X^3$, G, and A are as defined above, and
each W is independently various copolymer units.

6 Claims, No Drawings

POLY(METH)ACRYLAMIDES AND POLY(METH)ACRYLATES CONTAINING FLOURINATED AMIDE

BACKGROUND OF THE INVENTION

Various compositions are known to be useful as treating agents to provide surface effects to substrates. Surface effects include repellency to moisture, soil, and stains, and other effects, which are particularly useful for fibrous substrates and other substrates such as hard surfaces. Many such treating agents are fluorinated polymers or copolymers.

Most commercially available fluorinated polymers useful as treating agents for imparting repellency to substrates contain predominantly eight or more carbons in the perfluoroalkyl chain to provide the desired repellency properties. Honda et al, in Macromolecules, 2005, 38, 5699-5705 teach that for perfluoroalkyl chains of greater than 8 carbons, orientation of the $R_f$ groups is maintained in a parallel configuration while for such chains having less than 6 carbons, reorientation occurs, which decreases surface properties such as contact angle. Thus shorter chain perfluoroalkyls have traditionally not been successful commercially.

Various attempts have been made to improve particular surface effects and to increase the fluorine efficiency; i.e., boost the efficiency or performance of treating agents so that lesser amounts of the expensive fluorinated polymer are required to achieve the same level of performance or have better performance using the same level of fluorine. It is desirable to reduce the chain length of the perfluoroalkyl groups thereby reducing the amount of fluorine present, while still achieving the same or superior surface effects. U.S. Pat. No. 3,576,018 discloses fluorinated acrylamide monomers useful as oil and water repellent agents containing a perfluoroalkyl or fluorinated isoalkoxyalkyl having 3 to 17 carbon atoms. No polymers or copolymers are disclosed.

There is a need for polymer compositions which significantly improve the repellency and stain resistance of fluorinated polymer treating agents for fibrous substrates and hard surface substrates while using lower levels of fluorine. The present invention provides such compositions.

SUMMARY OF THE INVENTION

The present invention comprises a composition comprising a copolymer having repeating units in any sequence of Formula I

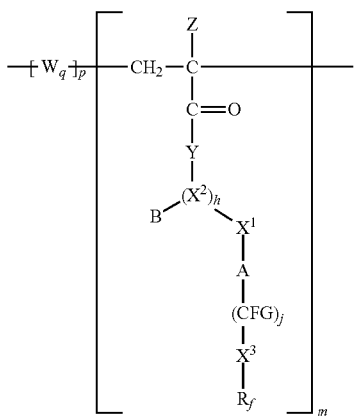

Formula 1 wherein
$R_f$ is a straight or branched perfluoroalkyl group having from about 1 to about 20 carbon atoms, or a mixture thereof, which is optionally interrupted by at least one oxygen atom,
$X^3$ is oxygen or $X^1$,
each $X^1$ is independently an organic divalent linking group having from about 1 to about 20 carbon atoms, optionally containing an oxygen, nitrogen, or sulfur, or a combination thereof,
G is F or $CF_3$,
A is an amide,
j is zero or positive integer,
$X^2$ is an organic linking group,
Y is O, N, or S,
h is zero when Y is N, and h is one when Y is O or S,
Z is H, a straight or branched alkyl group having from about 1 to about 4 carbon atoms, or halide,
B is H or

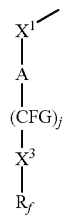

wherein
$R_f$, $X^1$, $X^3$, G, A, and j are as defined above, provided that when B is H, j is a positive integer,
m is a positive integer,
q is zero or a positive integer when Y is O, and q is a positive integer when Y is N or S,
p is zero or a positive integer when Y is O, and p is a positive integer when Y is N or S, and
each W is independently

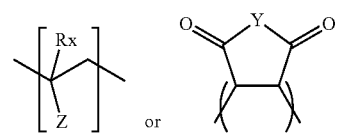

or $[R^1-X^1-Y-C(O)-C(Z)=CH_2]$,
wherein
$X^1$, Y, and Z are as defined above,
Rx is $C(O)O(R^1)$, $C(O)N(R^2)_2$, $OC(O)(R^1)$, $SO_2(R^1)$, $C_6(R^3)_5$, $O(R^1)$, halide, or $R^1$;
each $R^1$ is independently H, $C_nH_{2n+1}$, $C_nH_{2n}-CH(O)CH_2$, $[CH_2CH_2O]_iR^4$, $[C_nC_{2n}]N(R^4)_2$ or $[C_nH_{2n}]C_nF_{2n+1}$,
n is 1 to 40,
$R^4$ is H or $C_sH_{2s+1}$,
S=0 to 40,
i=1 to 200,
each $R^2$ is independently H, or $C_tH_{2t+1}$ wherein t is 1 to 20,
each $R^3$ is independently H, $COOR^1$, halogen, $N(R^1)_2$, $OR^1$, $SO_2NHR^1$, $CH=CH_2$, or $SO_3M$, wherein $R^1$ is as defined above, and
M is H, alkali metal salt, alkaline earth metal salt, or ammonium.

The present invention further comprises a composition comprising Formula 2

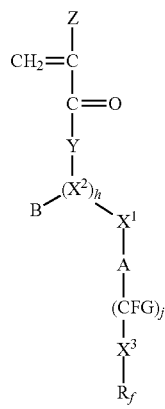

Formula 2 wherein $R_f$, $X^1$, $X^3$, G, j, A, Y, $X^2$, h, B, and Z are each defined as for Formula 1 above, provided that when Y is N or S, j is a positive integer.

The present invention further comprises a composition comprising Formula 3.

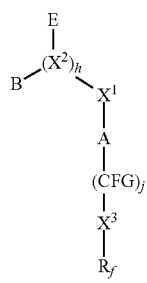

Formula 3 wherein $R_f$, $X^1$, $X^3$, G, j, A, B, $X^2$, and h are each defined as in Formula 2 above, and E is selected from the group consisting of hydroxyl, amine, halogen, and thiol, provided that h is zero when E is amine, and h is one when E is other than amine.

The present invention further comprises a method of providing water repellency and oil repellency to a substrate comprising contacting said substrate with a composition of Formula 1 as defined above.

The present invention further comprises a substrate to which has been applied a composition of Formula 1 as defined above.

DETAILED DESCRIPTION

All trademarks are denoted herein by capitalization. In all instances herein, the term "(meth)acrylate" is used to denote both acrylate or methacrylate. The term "(meth)acryloyl chloride" is used to denote both acryloyl chloride and methacryloyl chloride. The term "(meth)acrylamide" is used to denote both acrylamide or methacrylamide.

The present invention comprises a copolymer having repeating units in any sequence of Formula 1

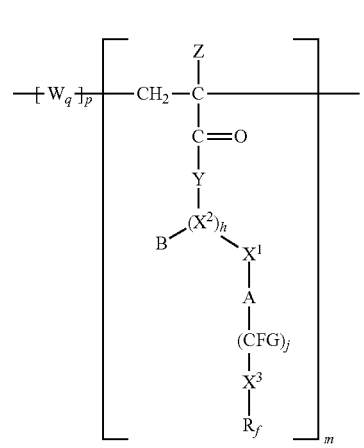

Formula 1 wherein $R_f$ is a straight or branched perfluoroalkyl group having from about 1 to about 20 carbon atoms, or a mixture thereof, which is optionally interrupted by at least one oxygen atom, $X^3$ is oxygen or $X^1$, each $X^1$ is independently an organic divalent linking group having from about 1 to about 20 carbon atoms, optionally containing an oxygen, nitrogen, or sulfur, or a combination thereof, G is F or $CF_3$, A is an amide, j is zero or positive integer, provided that when B is H, j is a positive integer, $X^2$ is an organic linking group, Y is O, N or S, h is zero when Y is N, and h is one when Y is O or S, Z is H, a straight or branched alkyl group having from about 1 to about 4 carbon atoms, or halide, B is H or

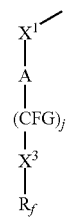

wherein $R_f$, $X^1$, $X^3$, G, j, and A are as defined above, provided that when B is H, j is a positive integer, m is a positive integer, q is zero or a positive integer when Y is O, and q is a positive integer when Y is N or S, p is zero or a positive integer when Y is O, and p is a positive integer when Y is N or S, each W is independently

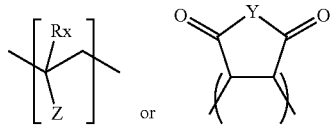

or [R$^1$—X$^1$—Y—C(O)—CH$_2$Z], wherein

X$^1$, Y, and Z are as defined above,

Rx is C(O)O(R$^1$), C(O)N(R$^2$)$_2$, OC(O)(R$^1$), SO$_2$(R$^1$), C$_6$(R$^3$)$_5$, O(R$^1$), halide, or R$^1$;

each R$^1$ is independently H, C$_n$H$_{2n+1}$, C$_n$H$_{2n}$—CH(O)CH$_2$, [CH$_2$CH$_2$O]$_i$R$^4$, [C$_n$C$_{2n}$]N(R$^4$)$_2$ or [C$_n$H$_{2n}$]C$_n$F$_{2n+1}$, n is 1 to 40, R$^4$ is H or C$_s$H$_{2s+1}$, s=0 to 40, i=1 to 200, each R$^2$ is independently H, or C$_t$H$_{2t+1}$ wherein t is 1 to 20, each R$^3$ is independently H, COOR$^1$, halogen, N(R$^1$)$_2$, OR$^1$, SO$_2$NHR$^1$, CH=CH$_2$, or SO$_3$M, and M is H, alkali metal salt, alkaline earth metal salt, or ammonium.

Preferably R$_f$ is a straight or branched perfluoroalkyl group having from about 1 to about 18 carbon atoms or a mixture thereof. More preferably R$_f$ is from about 1 to about 12 carbon atoms, or a mixture thereof. More preferably R$_f$ is from about 1 to about 6 carbon atoms, or a mixture thereof.

A is amide. In particular, A is —CONR$^5$— or —NR$^5$C(O)— wherein R$^5$ is H or alkyl.

Examples of suitable linking groups X$^1$ include straight chain, branched chain or cyclic alkylene, phenyl, arylene, arylalkylene, sulfonyl, sulfoxy, sulfonamido, carbonamido, carbonyloxy, urethanylene, ureylene (—NR$^5$CONR$^5$— wherein R$^5$ is H or alkyl), and combinations thereof such as sulfonamidoalkylene.

The copolymers of Formula 1 are prepared by polymerization of fluorinated amide-containing acrylic monomers, alkyl (meth)acrylate monomers and optionally other monomers. The copolymers of Formula 1 are prepared by reacting fluorinated (meth)acrylate or nonfluorinated (meth)acrylate with a fluorinated amide-containing fluorinated acrylic monomer of Formula 2:

Formula 2

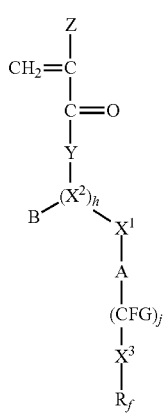

wherein

R$_f$, X$^1$, X$^3$, G, j, A, B, Y, X$^2$, h, and Z are each defined as for Formula 1 above, provided that, when Y is N or S, j is a positive integer.

The fluorinated amide-containing acrylic monomer of Formula 2, used in the preparation of the copolymer of Formula 1, is prepared by contacting acrylic acid, acrylate ester, or acryloyl chloride with a fluorochemical of Formula 3:

Formula 3

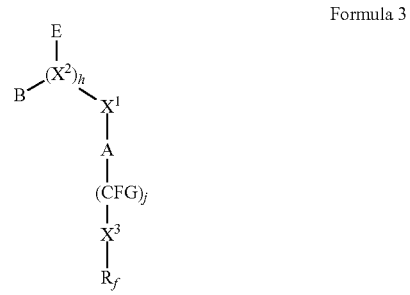

wherein

R$_f$ X$^1$, X$^3$, G, j, A, X$^2$, and h are each defined as in Formula 2 above, and E is selected from the group consisting of hydroxyl, amine, halogen, and thiol, provided that h is zero when E is amine, and h is one when E is other than amine. E is preferably hydroxyl or amine.

The preferred conditions for the reaction are at a temperature of from about 0° C. and about 60° C. Suitable solvents include tetrahydrofuran, methyl isobutyl ketone, acetone or ethyl acetate. A tertiary amine is used as a base to scavenge any acid chloride formed during the reaction.

The compound of Formula 3 is prepared by reaction between a perfluorinated ester (prepared according to reported methods in U.S. Pat. No. 6,054,615 and U.S. Pat. No. 6,376,705 each herein incorporated by reference) with a triamine or diamine alcohol with or without solvent. The conditions of this reaction are dependent on structure of the ester. The reaction of alpha, alpha-difluorosubstituted ester with diamine is conducted at a temperature of from about 5° C. to about 35° C. Suitable solvents for this reaction include tetrahydrofuran, methyl isobutyl ketone, acetone, CHCl$_3$, CH$_2$Cl$_2$, or ether. The reaction of ester without alpha-fluorine substitution with diamine is conducted at a temperature of from about 90° C. to about 160° C., preferably at between about 100° C. to about 140° C. Preferably no solvent is employed for this reaction, but suitable solvents include chlorobenzene, dimethylformamide, or 2-methoxyethyl ether.

The compound of Formula 3 is also prepared by reaction between a perfluorinated acyl fluoride with a diamine alcohol or amine alcohol. This reaction is conducted at a temperature of from about −30° C. to about 40° C., preferably at between about 5° C. to about 25° C. Suitable solvents for this reaction include tetrahydrofuran, methyl isobutyl ketone, acetone, CHCl$_3$, CH$_2$Cl$_2$, or 2-methoxyethyl ether, diethyl ether.

The fluorinated amide-containing fluorinated acrylic monomer of Formula 2 of the present invention is then polymerized with fluorinated (meth)acrylate or nonfluorinated (meth)acrylate to prepare the copolymer of Formula 1.

The nonfluorinated (meth)acrylate monomers suitable for use in the preparation of the copolymer of Formula 1 of the present invention comprise alkyl (meth)acrylates in which the alkyl group is a straight or branched chain containing 1 to about 20 carbon atoms, or mixtures thereof, preferably from about 1 to about 18 carbon atoms. The C$_1$-C$_{20}$ alkyl (meth)

acrylates (linear or branched) are exemplified by, but not limited to, alkyl (meth)acrylates where the alkyl group is methyl, ethyl, propyl, butyl, isoamyl, hexyl, cyclohexyl, octyl, 2-ethylhexyl, decyl, isodecyl, lauryl, cetyl, or stearyl. The preferred examples are 2-ethylhexyl acrylate, lauryl acrylate and stearyl acrylate.

Additional optional monomers can also be used in the polymerization reaction to prepare the copolymers of Formula 1 containing additional repeating units. These optional monomers include N-methylol (meth)acrylates, hydroxyalkyl (meth)acrylates, alkyloxy(meth)acrylates, fluorinated (meth)acrylates, glycidyl (meth)acrylates, stearyl acrylate, aminoalkyl methacrylate hydrochloride, acrylamide, alkyl acrylamide, vinyl acetate, vinyl stearate, alkyl vinyl sulfone, styrene, vinyl benzoic acid, alkyl vinyl ether, maleic anhydride, vinylidene chloride, vinyl chloride, and olefin.

Optional N-methylol monomers are exemplified by N-methylol acrylamide and N-methylol methacrylamide. The optional hydroxyalkyl (meth)acrylates have alkyl chain lengths in range between about 2 and about 4 carbon atoms, and are exemplified by 2-hydroxyethyl acrylate, 2-hydroxyethyl methacrylate. The optional alkyloxy(meth)acrylates also have alkyl chain lengths in range between about 2 and about 4 carbon atoms, and contain between 1 and about 12 oxyalkylene units per molecule, preferably between about 4 and about 10 oxyalkylene units per molecule, and most preferably between about 6 and about 8 oxyalkylene units per molecule, as determined by gas chromatography/mass spectrometry. Specific examples of the poly(oxyalkylene)(meth) acrylates are exemplified by, but not limited to, the reaction product of 2-hydroxyethyl methacrylate ethylene oxide. The reaction with nine moles pf ethylene oxide yields 2-hydroxyethyl methacrylate/9-ethylene oxide adduct, and the reaction with six moles of ethylene oxide yields 2-hydroxyethyl methacrylate/6-ethylene oxide adduct. Other optional nonfluorinated monomers can be styrene, maleic anhydride, and vinylidene chloride. When such optional monomers are present, polymerization processes employed are conventional ones known to those skilled in the art.

The fluorinated copolymers of Formula 1 of this invention are prepared in organic solvent by free radical initiated polymerization of a mixture of fluorinated amide-containing acrylic monomers of Formula 2 with a (meth)acrylate, and, any of the optional monomers listed above. The fluorinated copolymers of this invention are made by agitating the monomers described above in organic solvent in a suitable reaction vessel which is equipped with an agitation device and an external heating and cooling device. A free radical initiator is added and the temperature rose to from about 40° to about 60° C. A polymerization regulator or chain transfer agent may be added to control molecular weight of the resultant polymer. The polymerization initiator is exemplified by [2,2'-azobis(2, 4-dimethylpentanenitrile)]. These initiators are sold by E. I. du Pont de Nemours and Company, Wilmington, Del., commercially under the name of "VAZO". An example of the polymerization regulator or chain transfer agent is dodecylmercaptan. Suitable organic solvents useful in the preparation of the copolymers of Formula 1 of the present invention include tetrahydrofuran, acetone, methyl isobutyl ketone, isopropanol, ethyl acetate, and mixtures of them. Tetrahydrofuran is preferred. The reaction is conducted under an inert gas, such as nitrogen, to the exclusion of oxygen. The solution can be retained for dilution and application to the substrate. Alternatively, the polymer can be isolated by precipitation with methanol, then dissolves in suitable solvent, such as tetrahydrofuran for application to the substrate. The product of the reaction is a fluorinated amide-containing copolymer of Formula 1.

The fluorinated amide-containing copolymer of Formula 1 can be made using from about 25 to about 80 weight percent fluorinated amide-containing acrylate of Formula 2, from about 1 to about 40 weight percent (meth)acrylate, and from 0 to about 75 weight percent optional monomers.

The resulting fluorinated amide-containing copolymer of Formula 1 is then poured into water. The collected polymer is dissolved in a solvent selected from the groups comprising simple alcohols, ketones or tetrahydrofuran that are suitable as the solvent for final application to substrates (hereinafter the "application solvent"). The final product for application to a substrate is a solution of the fluorinated amide-containing copolymer of Formula 1.

The present invention further comprises a composition of Formula 2 as defined above wherein $R_f$ is linear. This composition is prepared as described above by contacting acrylic acid, acrylate ester, or acryloyl chloride with a fluorochemical of Formula 3 as defined above wherein $R_f$ is linear. This composition is useful for the preparation of a composition of Formula 1 wherein $R_f$ is linear.

The present invention further comprises a composition of Formula 3 as defined above wherein $R_f$ is linear. This composition is prepared as described above by the reaction of a triamine or diamine alcohol with a perfluorinated ester wherein the perfluoro group is linear. This composition is useful for preparing a composition of Formula 2 wherein $R_f$ is linear.

The present invention further comprises a method of providing oil repellency and water repellency to a substrate comprising contacting the fluorinated amide-containing copolymer solutions of Formula 1 of the present invention with the substrate. Suitable substrates include fibrous or hard surface substrates as defined below. The contacting is conducted using conventional techniques. The copolymer of Formula 1 is effectively applied to fibrous substrates by a wide variety of methods known to those skilled in the art, such as: padding, spraying, foaming in conjunction with foaming agents, flexnip, nip, kiss-roll, exhaustion, beck, skein, winch, liquid injection, overflow flood, exhaust in beck dyeing equipment, or continuous exhaust during a continuous dyeing operation. It is applied by such methods to dyed or undyed substrates. For hard surface substrates application techniques include, for example, by brushes, rollers, paint pads, mats, sponges, combs, hand-operated pump dispensers, compressed air operated spray guns, electric or electrostatic atomizers, backpack spray application equipment, clothes, papers, feathers, styluses, knives, and other conventional applicator tools. If dipping is used as a method to apply the copolymer, no special equipment is required.

The fluorinated amide-containing copolymer solution of Formula 1 of this invention is applied to the substrate as such, or in combination with other optional textile finishes or surface treating agents. Such optional additional components include treating agents or finishes to achieve additional surface effects, or additives commonly used with such agents or finishes. Such additional components comprise compounds or compositions that provide surface effects such as no iron, easy to iron, shrinkage control, wrinkle free, permanent press, moisture control, softness, strength, anti-slip, anti-static, anti-snag, anti-pill, stain repellency, stain release, soil repellency, soil release, water repellency, oil repellency, odor control, antimicrobial, sun protection, and similar effects. One or more such treating agents or finishes can be applied to the substrate before, after, or simultaneously with the copolymer of the present invention. For example for fibrous substrates, when synthetic or cotton fabrics are treated, use of a wetting agent can be desirable, such as ALKANOL 6112 available from E. I. du Pont de Nemours and Company, Wilmington, Del. When cotton or cotton-blended fabrics are treated, a wrinkle-resistant resin can be used such as PERMAFRESH EFC available from Omnova Solutions, Chester, S.C.

Other additives commonly used with such treating agents or finishes may also be present such as surfactants, pH adjusters, cross linkers, wetting agents, wax extenders, and other additives known by those skilled in the art. Suitable surfactants include anionic, cationic, and nonionic. Preferred is an anionic surfactant such as sodium lauryl sulfonate, available as DUPONOL WAQE from Witco Corporation, Greenwich, Conn. Examples of such finishes or agents include processing aids, foaming agents, lubricants, anti-stains, and the like. The composition is applied at a manufacturing facility, retailer location, or prior to installation and use, or at a consumer location.

Application rates for the fluorinated amide-containing copolymer solution of Formula 1 of the present invention are in the range of from about 10 to about 1000 g/m$^2$ depending on the substrate porosity. A treated fibrous substrate typically has a fluorine content of from about 0.05% to about 1.0% by weight. Generally, higher levels of fluorine provide greater oil repellency and water repellency, but become economically unfeasible. The fluorine loading is optimized depending upon type of substrate.

The optimal repellent treatment for a given substrate depends on (1) the characteristics of the fluorinated copolymer, (2) the characteristics of the surface of the substrate, (3) the amount of fluorinated copolymer applied to the surface, (4) the method of application of the fluorinated copolymer onto the surface, and many other factors. Some fluorinated copolymer repellents work well on many different substrates and are repellent to oil, water, and a wide range of other liquids. Other fluorinated copolymer repellents exhibit superior repellency on some substrates or require higher loading levels.

The present invention further comprises substrates treated with the fluorinated amide-containing fluorinated copolymer solution of Formula 1 of the present invention. Suitable substrates include fibrous or hard surface substrates. The fibrous substrates include woven and nonwoven fibers, fabrics, fabric blends, textiles, nonwovens, paper, leather, and carpets. These are made from natural or synthetic fibers including cotton, cellulose, wool, silk, polyamide, polyester, polyolefin, polyacrylonitrile, polypropylene, rayon, nylon, aramid, and acetate or blends thereof. By "fabric blends" is meant fabric made of two or more types of fibers. Typically these blends are a combination of at least one natural fiber and at least one synthetic fiber, but also can include a blend of two or more natural fibers or of two or more synthetic fibers. These substrates are often used in a wide variety of uses including, for example, textiles, clothing, furnishings, and carpets. The hard surface substrates include porous and non-porous mineral surfaces, such as glass, stone, masonry, concrete, unglazed tile, brick, porous clay and various other substrates with surface porosity. Specific examples of such substrates include unglazed concrete, brick, tile, stone (including granite and limestone), grout, mortar, marble, limestone, statuary, monuments, wood, composite materials such as terrazzo, and wall and ceiling panels including those fabricated with gypsum board. These are used in the construction of buildings, roads, parking ramps, driveways, floorings, fireplaces, fireplace hearths, counter tops, and other decorative uses in interior and exterior applications. The substrates of the present invention have excellent water repellency and oil repellency.

The fluorinated amide-containing copolymer compositions of the present invention having a perfluoroalkyl chain of 1 to about 20 carbons are useful to provide one or more of excellent water repellency and oil repellency to treated substrates. The fluorinated amide-containing copolymers of the present invention allow for the use of shorter perfluoroalkyl groups containing 6 or fewer carbon atoms while conventional commercially available acrylates typically show poor oil repellency and water repellency performance if the perfluoroalkyl groups contain less 8 carbon atoms.

Materials and Test Methods

Tetrahydrofuran (THF) and stearyl methacrylate (SMA) were obtained from Sigma-Aldrich, St. Louis, Mo. THF is used in the Examples herein to designate tetrahydrofuran.

Perfluoro-2-methyl-3-oxahexanoyl fluoride and $CF_3(OCF_2)_nCO_2CH_3$ were obtained from E. I. du Pont de Nemours and Company, Wilmington, Del.

Cotton fabric was 100% Levi's cotton (medium tan) from INVISTA, Wilmington, Del.

100% Nylon fabric was from Burlington Industries (ITG), Greensboro, N.C.

Test Method 1—Fibrous Substrate Treatment

The fibrous substrate, for example fabric, was treated with the copolymer dispersion or solution using a following process. Copolymer solutions were prepared in tetrahydrofuran to contain 2000 mg/kg of fluorine. The solutions were applied to cotton and nylon substrates by pipetting the copolymer solution the substrates to saturation. After application, the substrate was dried in air and cured at approximately 150° C. for about 2 minutes. The substrate was allowed to cool down to room temperature before the oil and water repellency measurements were conducted.

Test Method 2—Water Repellency

The water repellency of a treated substrate was measured according to AATCC standard Test Method No. 193-2004 and the DuPont Technical Laboratory Method as outlined in the TEFLON Global Specifications and Quality Control Tests information packet. The test determines the resistance of a treated substrate to wetting by aqueous liquids. Drops of water-alcohol mixtures of varying surface tensions are placed on the substrate and the extent of surface wetting is determined visually. The test provides a rough index of aqueous stain resistance.

The composition of water repellency test liquids is shown in table 1.

TABLE 1

Water Repellency Test Liquids

| Water Repellency Rating Number | Composition, Isopropyl Alcohol | Vol % Distilled Water |
|---|---|---|
| 1 | 2 | 98 |
| 2 | 5 | 95 |
| 3 | 10 | 90 |
| 4 | 20 | 80 |
| 5 | 30 | 70 |
| 6 | 40 | 60 |
| 7 | 50 | 50 |
| 8 | 60 | 40 |
| 9 | 70 | 30 |
| 10 | 80 | 20 |
| 11 | 90 | 10 |
| 12 | 100 | 0 |

Testing Procedure:

Three drops of Test Liquid 1 are placed on the treated substrate. After 10 seconds, the drops are removed by using vacuum aspiration. If no liquid penetration or partial absorption (appearance of a darker wet patch on the substrate) is observed, the test is repeated with Test Liquid 2. The test is repeated with Test Liquid 3 and progressively higher Test Liquid numbers until liquid penetration (appearance of a darker wet patch on the substrate) is observed. The test result is the highest Test Liquid number that does not penetrate into the substrate. Higher scores indicate greater repellency.

Test Method 3—Oil Repellency

The treated fabric samples were tested for oil repellency by a modification of AATCC standard Test Method No. 118, conducted as follows. A fabric sample is treated with a polymer solution as previously described. A series of organic liquids, identified below in Table 2, are then applied drop wise to the fabric samples. Beginning with the lowest numbered test liquid (Repellency Rating No. 1), one drop (approximately 5 mm in diameter or 0.05 mL volume) is placed on each of three locations at least 5 mm apart. The drops are observed for 30 seconds. If, at the end of this period, two of the three drops are still spherical in shape with no wicking around the drops, three drops of the next highest numbered liquid are placed on adjacent sites and similarly observed for 30 seconds. The procedure is continued until one of the test liquids results in two of the three drops failing to remain spherical to hemispherical, or wetting or wicking occurs.

The oil repellency rating of the fabric is the highest numbered test liquid for which two of the three drops remained spherical to hemispherical, with no wicking for 30 seconds. In general, treated fabrics with a rating of 5 or more are considered good to excellent; fabrics having a rating of one or greater can be used in certain applications.

The treated samples of hard surface substrates were tested for oil repellency by a modification of AATCC standard Test Method No. 118, conducted as follows. Three drops of Test Oil 1 in Table 2 are placed on the treated substrate. After 30 s, the drops are removed by using vacuum aspiration. If no liquid penetration or partial absorption (appearance of a darker wet patch on the substrate) is observed, the test is repeated with Test Oil 2. The test is repeated with Test Oil 3 and progressively higher Test Oil numbers until liquid penetration (appearance of a darker wet patch on the substrate) is observed. The test result is the highest Test Oil number that does not show liquid penetration into the substrate. Higher scores indicate greater repellency.

TABLE 2

Oil Repellency Test Liquids

| Oil Repellency Rating Number | Test Solution |
|---|---|
| 1 | NUJOL Purified Mineral Oil |
| 2 | 65/35 NUJOL/n-hexadecane by volume at 21° C. |
| 3 | n-hexadecane |
| 4 | n-tetradecane |
| 5 | n-dodecane |
| 6 | n-decane |
| 7 | n-octane |
| 8 | n-heptane |

Note:
NUJOL is a trademark of Plough, Inc., for a mineral oil having a Saybolt viscosity of 360/390 s at 38° C. and a specific gravity of 0.880/0.900 at 15° C.

EXAMPLES

Example 1

A 50-mL flask was charged with methyl 2,2,3,3-tetrahydroperfluorononanoate (9.0 g, prepared according to the procedure in U.S. Pat. No. 6,054,615) and 1,3-diamino-2-propanol (1.0 g). The resulting mixture was allowed to stir at 140° C. for 8 h. The reaction mixture solidified after being cooled to room temperature and dried on full vacuum for 8 h to give a solid (8.95 g). The product was N,N'-bis(2,2,3,3-tetrahydroperfluorononanoyl)-1,3-diamino-2-propanol as shown by the following analyses. H NMR (CDCl$_3$) 2.52 (m, 9H), 3.36 (m, 4H), 3.80 (quintet, J=5 Hz, 1H), 6.36 (br s, 2H) ppm. F NMR −81.2 (tt, J=10, 3 Hz, 6F), −114.9 (m, 4F), −122.3 (m, 4F), −123.3 (m, 4F), −123.9 (m, 4F), −126.5 (m, 4F) ppm. For HNMR and FNMR for this and all examples herein, ppm indicates one part per one million parts in frequency shift.

A 25-mL flask was charged with N,N'-bis(2,2,3,3-tetrahydroperfluorononanoyl)-1,3-diamino-2-propanol (6.0 g.) prepared according to the above procedure, triethylamine (1.42 g), and tetrahydrofuran (20 mL). Methacryloyl chloride (1.45 g) in tetrahydrofuran (3 mL) was added drop wise to the above mixture at about 10° C. The mixture was stirred at room temperature for 15 h. The mixture was poured into water (40 mL) and extracted with ether (2×100 mL). The ether solution was washed with water (3×50 mL), Saturated NaCl solution (10 mL), dried over Na$_2$SO$_4$, concentrated, and dried on vacuum to give 6.35 g wax product. The product is N,N'-bis (2,2,3,3-tetrahydroperfluorononanoyl)-1,3-diamino-2-propyl methacrylate.

A mixture of N,N'-bis(2,2,3,3-tetrahydroperfluorononanoyl)-1,3-diamino-2-propyl methacrylate (2.0 g), stearyl methacrylate (0.8 g), 2,2'-azobis(2,4-dimethylpentanenitrile) (VAZO 52) (25 mg), and tetrahydrofuran (5 mL) was heated to 60° C. for 15 h. The mixture was poured into methanol (100 mL). The precipitated polymer was washed with methanol (2×30 mL), dried on vacuum to give a polymer (1.28 g). It was a copolymer and contained about 38.7% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 2

A 100-mL bottle was charged with diethylenetriamine (6.64 g) and 52.6 g of methyl 2,2,3,3-tetrahydroperfluorononanoate (prepared according a procedure from U.S. Pat. No. 6,054,615). The resulting mixture was heated to 120° C. for 20 h. The reaction mixture was dried on vacuum at 70° C. for 2 h to give a solid (54 g). The product is 1,7-bis(2,2,3,3-tetrahydroperfluorononanoyl)-1,4,7-triazaheptane as shown by the following analyses. H NMR (CDCl$_3$): 1.66 (br s, 1H), 2.51 (m, 8H), 2.78 (t, J=6 Hz, 4H), 3.35 (q, J=6 Hz, 4H), 6.20 (br s, 2H) ppm. F NMR (CDCl$_3$): −81.2 (tt, J=10, 3 Hz, 6F), −115.1 (m, 4F), −122.4 (m, 4F), −123.4 (m, 4F), −124.0 (m, 4F), −126.6 (m, 4F) ppm.

A 100-mL flask was charged with 1,7-bis(2,2,3,3-tetrahydroperfluorononanoyl)-1,4,7-triazaheptane (15.7 g), triethylamine (2.49 g), and tetrahydrofuran (22 mL). Methacryloyl chloride (2.58 g dissolved in 7 mL of tetrahydrofuran) was added drop wise to the above mixture at about 10° C. The mixture was stirred at room temperature for 2 h. The reaction mixture was poured into water (200 mL) and extracted with methylene chloride (250 mL). The methylene chloride extract was washed with water (3×50 mL). The original aqueous layer was extracted with ether (200 mL) and this ether extract was washed with water (3×50 mL) and saturated NaCl solution. The combined methylene chloride and solution were dried over $Na_2SO_4$, concentrated, and dried on vacuum to give a solid (14.8 g). The product is 1,7-bis(2,2,3,3-tetrahydroperfluorononanoyl)-4-methacryloyl-1,4,7-triazaheptane as shown by the following analyses. H NMR ($CDCl_3$): 1.89 (m, 3H), 2.51 (m, 8H), 3.55 (m, 8H), 4.90 (m, 1H), 5.16 (m, 1H), 6.31 (br s, 1H), 7.51 (br s, 1H) ppm. F NMR ($CDCl_3$): −81.3 (t, J=10 Hz, 6F), −115.1 (m, 4F), −122.4 (m, 4F), −123.4 (m, 4F), −124.0 (m, 4F), −126.6 (m, 4F) ppm.

A mixture of stearyl methacrylate (1.6 g), 1,7-bis(2,2,3,3-tetrahydroperfluorononanoyl)-4-methacryloyl-1,4,7-triazaheptane (4.0 g), tetrahydrofuran (10 mL), and 2,2'-azobis(2,4-dimethylpentanenitrile) (45 mg) was heated to 60° C. for 36 h. The mixture was poured into methanol (100 mL). The precipitated polymer was washed with methanol (2×30 mL), dried on vacuum to give a solid (1.85 g). It was a copolymer and contained about 9.4% fluorine.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 3

A 25-mL bottle was charged with 1,3-diamino-2-propanol (0.61 g) and tetrahydrofuran (4 mL). Ethyl 3,3,4,4-tetrahydroperfluorooctanoate (5.0 g), (prepared according a procedure from U.S. Pat. No. 6,376,705), in tetrahydrofuran (2 mL) was added drop wise at about 10° C. The resulting mixture was allowed to stir for 15 h at room temperature. The reaction mixture was concentrated and dried on vacuum to give 5.0 g of solid. The product is N,N'-bis(3,3,4,4-tetrahydroperfluorooctanoyl)-1,3-diamino-2-propanol as show by the following analyses. H NMR ($CDCl_3$) 1.53 (br s, 1H), 2.41 (m, 8H), 3.45 (m, 4H), 3.97 (Quintet, J=5 Hz, 1H), 6.99 (br. s, 2H) ppm. F NMR −81.5 (tt, J=10, 3 Hz, 6F), −107.1 (m, 4F), −115.1 (m, 4F), −124.7 (m, 4F), −126.4 (m, 4F) ppm.

A 50-mL flask was charged with N,N'-bis(3,3,4,4-tetrahydroperfluorooctanoyl)-1,3-diamino-2-propanol (4.8 g) prepared according to the above procedure, triethylamine (0.80 g), and tetrahydrofuran (20 mL). Methacryloyl chloride (0.82 g) in tetrahydrofuran (3 mL) was added drop wise to the above mixture at room temperature. The mixture was stirred at room temperature for 15 h. GC analysis of the reaction mixture indicated the formation of the product and about 4% of starting alcohol. Methacryloyl chloride (0.1 g) and triethylamine (0.10 g) were added to the reaction mixture. The resulting mixture was stirred at 35° C. for another 15 h. The reaction mixture was concentrated and dried on vacuum to give 5.0 g of solid. The product is N,N'-bis(3,3,4,4-tetrahydroperfluorooctanoyl)-1,3-diamino-2-propyl methacrylate as shown by the following analyses. H NMR (tetrahydrofuran-d8) 2.00 (m, 3H), 2.54 (m, 8H), 3.60 (m, 4H), 5.26 (m, 1H), 5.69 (m, 1H), 6.19 (m, 1H), 8.45 (br. s, 2H) ppm. F NMR −81.5 (tt, J=10, 3 Hz, 6F), −106.9 (ABq t, J=258, 15 Hz, 4F), −114.7 (m, 4F), −124.2 (m, 4F), −126.1 (m, 4F) ppm.

A mixture of N,N'-bis(3,3,4,4-tetrahydroperfluorooctanoyl)-1,3-diamino-2-propyl methacrylate (2.0 g), stearyl methacrylate (0.80 g), 2,2'-azobis(2,4-dimethylpentanenitrile) (25 mg), and tetrahydrofuran (5 mL) was heated to 60° C. for 15 h. The mixture was poured into methanol (100 mL). The precipitated polymer was washed with methanol (2×30 mL), dried on vacuum to give a white solid (2.44 g). It was a copolymer and contained about 44.6% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 4

A 25-mL bottle was charged with diethylenetriamine (0.85 g) and tetrahydrofuran (4 mL). Ethyl 3,3,4,4-tetrahydroperfluorooctanoate (6.25 g, prepared according a procedure from U.S. Pat. No. 6,376,705), in tetrahydrofuran (2 mL) was added drop wise at about 10° C. The resulting mixture was allowed to stir for 15 h at room temperature. The reaction mixture was concentrated and dried on vacuum to give 6.27 g of solid. The product is 1,7-bis(2,2,3,3-tetrahydroperfluorooctanoyl)-1,4,7-triazaheptane as shown by the following analyses. H NMR ($CDCl_3$) 1.55 (br s, 1H), 2.39 (m, 8H), 2.85 (t, J=6 Hz, 4H), 3.42 (q, J=6 Hz, 4H), 6.80 (br. s, 2H) ppm. F NMR −81.5 (tt, J=10, 3 Hz, 6F), −107.3 (t, J=16 Hz, 4F), −115.2 (m, 4F), −124.8 (m, 4F), −126.5 (m, 4F) ppm.

A 25-mL flask was charged with 1,7-bis(2,2,3,3-tetrahydroperfluorooctanoyl)-1,4,7-triazaheptane (3 g), triethylamine (0.49 g), and tetrahydrofuran (5 mL). Methacryloyl chloride (0.50 g) in tetrahydrofuran (2 mL) was added drop wise to the above mixture at about 10° C. The mixture was stirred at room temperature for 3 h. The reaction mixture was pored into water (40 mL) and extracted with methylene chloride (50 mL). The organic layer was washed with water (2×30 mL), dried over $Na_2SO_4$, concentrated and dried on vacuum to give a wax product (3.3 g). The product is 1,7-bis(2,2,3,3-tetrahydroperfluorooctanoyl)-4-methacryloyl-1,4,7-triazaheptane as shown by the following analyses. H NMR ($CDCl_3$) 1.93 (s, 3H), 2.38 (m, 8H), 3.57 (m, 4H), 3.62 (m, 4H), 5.01 (m, 1H), 5.22 (m, 1H), 6.23 (br. s, 2H) ppm. F NMR −81.5 (tt, J=10, 3 Hz, 6F), −107.3 (m, 4F), −115.2 (m, 4F), −124.7 (m, 4F), −126.5 (m, 4F) ppm.

A mixture of 1,7-bis(2,2,3,3-tetrahydroperfluorooctanoyl)-4-methacryloyl-1,4,7-triazaheptane (2.0 g), stearyl methacrylate (0.8 g), 2,2'-azobis(2,4-dimethylpentanenitrile) (25 mg), and tetrahydrofuran (3 mL) was heated to 60° C. for 15 h. The mixture was poured into methanol (100 mL). The precipitated polymer was washed with methanol (2×30 mL), dried on vacuum to give a white solid (0.85 g). It was a copolymer and contained about 5.1% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 5

A 25-mL bottle was charged with 1,3-diamino-2-propanol (0.5 g) and tetrahydrofuran (2 mL). Ethyl 3,3,4,4-tetrahydroperfluorodecanoate (5.45 g), (prepared according a procedure from U.S. Pat. No. 6,376,705), in tetrahydrofuran (2 mL) was added drop wise at about 15° C. The resulting mixture was allowed to stir for 3 hours at room temperature then at 50° C. for 2 h. The reaction mixture was concentrated and dried on vacuum to give 5.08 g of white solid, yield about 96%. The product is N,N'-bis(3,3,4,4-tetrahydroperfluorodecanoyl)-1,3-diamino-2-propanol as shown by the following analyses. H NMR 2.49 (m, 8H), 2.78 (br s, 1H), 3.37 (m, 4H), 3.95 (quintet, J=6 Hz, 1H), 8.07 (br s, 2H) ppm. F NMR −82.2 (tt, J=10, 3 Hz, 6F), −107.9 (m, 4F), −115.3 (m, 4F), −122.9 (m, 4F), −123.8 (m, 4F), −124.2 (m, 4F), −127.2 (m, 4F) ppm.

A 25-mL flask was charged with N,N'-bis(3,3,4,4-tetrahydroperfluorodecanoyl)-1,3-diamino-2-propanol (2.0 g), triethylamine (0.33 g), and tetrahydrofuran (3 mL). Methacryloyl chloride (0.33 g) in tetrahydrofuran (3 mL) was added drop wise at about 10° C. The resulting mixture was allowed to stir for 15 h at room temperature. The resulting solids were removed by filtration and washed with about 50 mL of methylene chloride. The combined filtrate and washings were then poured into about 25 mL water. The organic layer was isolated and washed again with water (2×30 mL), dried over $Na_2SO_4$, concentrated, and dried under vacuum over night to give a solid (2.03 g). The product is N,N'-bis(3,3,4,4-tetrahydroperfluorodecanoyl)-1,3-diamino-2-propyl methacrylate as shown by the following analyses. F NMR (acetone-d6) −82.2 (tt, J=10, 3 Hz, 6F), −107.8 (ABq m, J=255 Hz, 4F), −122.9 (m, 4F), −123.8 (m, 4F), −124.2 (m, 4F), −127.2 (m, 4F) ppm. H NMR (acetone-d6) 1.89 (m, 3H), 2.47 (m, 8H), 3.36 (m, 4H), 5.22 (m, 1H), 5.62 (m, 1H), 6.08 (m, 1H), 8.39 (br s, 2H) ppm.

A mixture of N,N'-bis(3,3,4,4-tetrahydroperfluorodecanoyl)-1,3-diamino-2-propyl methacrylate (2.0 g), stearyl methacrylate (1.2 g), 2,2'-azobis(2,4-dimethylpentanenitrile) (25 mg), and tetrahydrofuran (10 mL) was heated at 60° C. for 15 h. The reaction mixture was poured into methanol (80 mL). The polymer was precipitated and washed with methanol (20 mL), then dried on vacuum to give a white solid (2.36 g). It was a copolymer and contained about 34% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 6

A 25-mL bottle was charged with diethylenetriamine (1.1 g) and tetrahydrofuran (5 mL). Ethyl 3,3,4,4-tetrahydroperfluorodecanoate (10 g, prepared according a procedure from U.S. Pat. No. 6,376,705) in tetrahydrofuran (4 mL) was added drop wise at about 15° C. The resulting mixture was allowed to stir for 15 h at room temperature. The reaction mixture was concentrated and dried on vacuum to give 10 g of solid. The product is 1,7-bis(2,2,3,3-tetrahydroperfluorodecanoyl)-1,4,7-triazaheptane as shown by the following analyses. H NMR ($CDCl_3$) 1.28 (br s, 1H), 2.39 (m, 8H), 2.85 (t, J=5 Hz, 4H), 3.42 (q, J=5 Hz, 4H), 6.79 (br. s, 2H) ppm. F NMR −81.3 (tt, J=10, 3 Hz, 6F), −107.4 (t, J=16 Hz, 4F), −115.0 (m, 4F), −122.4 (m, 4F), −123.3 (m, 4F), −123.8 (m, 4F), −126.6 (m, 4F) ppm.

A 25-mL flask was charged with 1,7-bis(2,2,3,3-tetrahydroperfluorodecanoyl)-1,4,7-triazaheptane (5 g), triethylamine (0.64 g), and tetrahydrofuran (15 mL). Methacryloyl chloride (0.67 g) in tetrahydrofuran (3 mL) was added drop wise to the above mixture at about 10° C. The mixture was stirred at room temperature for 15 h. The reaction mixture was poured into water (50 mL) and extracted with methylene chloride (100 mL). The organic layer was washed with water (2×50 mL). During second wash, the organic layer became gel. The gel was isolated and dried in air to give 4.9 g solid. The product is 1,7-bis(2,2,3,3-tetrahydroperfluorodecanoyl)-4-methacryloyl-1,4,7-triazaheptane as shown by the following analyses. H NMR (THF-d8) 2.00 (m, 3H), 2.52 (m, 8H), 3.55 (m, 4H). 3.67 (m, 4H), 5.12 (m, 1H), 5.23 (m, 1H), 8.41 (br s, 2H) ppm. F NMR (THF-d8) −81.5 (tt, J=10 Hz, 6F), −107.2 (m, 4F), −114.8 (m, 4F), −122.2 (m, 4F), −123.1 (m, 4F), −123.6 (m, 4F), −126.5 (m, 4F) ppm.

A mixture of 1,7-bis(2,2,3,3-tetrahydroperfluorodecanoyl)-4-methacryloyl-1,4,7-triazaheptane (2.0 g), stearyl methacrylate (0.8 g), 2,2'-azobis(2,4-dimethylpentanenitrile) (25 mg), and tetrahydrofuran (3 mL) were heated to 60° C. for 24 h. The reaction mixture was poured into methanol (100 mL). The precipitated polymer was washed with methanol (2×30 mL) and dried under vacuum to give a white solid (0.81 g). It was a copolymer and contained about 5.6% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 7

A mixture of N,N'-bis(2,2,3,3-tetrahydroperfluorononanoyl)-1,3-diamino-2-propyl acrylate (2.0 g), stearyl methacrylate (0.8 g), 2,2'-azobis(2,4-dimethylpentanenitrile) (35 mg), and tetrahydrofuran (5 mL) was heated to 60° C. for 15 h. The mixture was poured into methanol (100 mL). The precipitated polymer was washed with methanol (2×20 mL) and dried on vacuum to give a solid (2.48 g). It was a copolymer and contained about 32.7% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 8

A mixture of N,N'-bis(2,2,3,3-tetrahydroperfluorononanoyl)-1,3-diamino-2-propyl methacrylate (1.8 g), styrene (0.88 g), 2,2'-azobis(2,4-dimethylpentanenitrile) (25 mg), and tetrahydrofuran (5 mL) was heated to 60° C. for 15 h. The mixture was poured into methanol (100 mL). The precipitated polymer was washed with methanol (2×30 mL), dried on vacuum to give a solid (1.56 g). It was a copolymer and contained about 38% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 9

A 25-mL flask was charged with 1,3-diamino-2-propanol (1.5 g) and THF (5 mL). $CF_3(OCF_2)_nCO_2Me$ (n: 2-5, 14.5 g) in THF (5 mL) was added drop wise at about 10° C. The resulting mixture was allowed to stir for 15 h at room temperature. The reaction mixture was concentrated and dried on vacuum to give 13.5 g of viscous oil, having H NMR ($CDCl_3$) 1.55 (br s, 1H), 3.41 (m, 4H), 4.02 (Quintet, J=5 Hz, 1H), 6.95 (br. s, 2H) ppm. The product is N,N'-bis(polyoxaperfluoroacyl)-1,3-diamino-2-propanol.

A 25-mL flask was charged with N,N'-bis(polyoxaperfluoroacyl)-1,3-diamino-2-propanol (5.5 g, E110448-72), $Et_3N$ (0.82 g), and THF (15 mL). Methacryloyl chloride (0.84 g in 3 mL of THF) was added drop wise to the above mixture at about 10° C. The mixture was stirred at room temperature for 15 h. GC analysis of the reaction mixture indicated the formation of the product. The mixture was poured into water (40 mL) and extracted with ether (100 mL). The ether solution was washed with water (3×30 mL), NaCl (saturated, 10 mL), dried over $Na_2SO_4$, concentrated and dried on vacuum to give 5.7 g of a very viscous oil. The product is N,N'-bis(polyoxaperfluoroacyl)-1,3-diamino-2-propyl methacrylate.

A mixture of N,N'-bis(polyoxaperfluoroacyl)-1,3-diamino-2-propyl methacrylate (2.0 g), stearyl methacrylate (0.80 g), VAZO 52 (25 mg), and THF (5 mL) was heated to 60° C. for 15 h. The mixture was poured into methanol (100 mL). The precipitated polymer was washed with methanol (2×30 mL), dried under vacuum to give a white solid (1.01 g). It was a copolymer and contained about 23.7% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 10

A 100-mL flask was charged with ethanolamine (2.0 g) and THF (20 mL). $CF_3(OCF_2)_nCO_2Me$ (n: 2-5, 10 g) was added drop wise to the above mixture at room temperature. A slightly exothermic reaction was observed. The mixture was stirred at room temperature for 1 h. GC analysis of the mixture indicated that the desired amides were formed. The reaction mixture was allowed to stir at room temperature over night. The reaction mixture was poured into water (150 mL) and extracted with $CH_2Cl_2$ (100 mL). The extract was washed with water (3×50 mL) and concentrated, dried on vacuum to give an oil (9.5 g), having H NMR ($CDCl_3$) 1.77 (br s, 1H), 3.54 (q, J=5 Hz, 2H), 3.92 (t, J=5 Hz, 2H), 6.74 (br s, 1H) ppm. The product is N-(polyoxaperfluoroacyl)-2-aminoethanol.

A 100-mL flask was charged with triethylamine (3.0 g), THF (60 mL), and N-(polyoxaperfluoroacyl)-2-aminoethanol (9.1 g). Methacryloyl chloride (3.1 g in THF 20 mL) was added drop wise to the above mixture at 10° C. The mixture was stirred at room temperature for 3 h. The solid was removed by filtration and the filtrate was poured into water (150 mL) and extracted with $CH_2Cl_2$ (2×100 mL). The extracts were washed with water (3×50 mL) and concentrated, dried on vacuum to give oil (10.3 g). It is N-(polyoxaperfluoroacyl)-2-aminoethyl methacrylate.

In a dry box, a 25-mL flask was charged with VAZO 52 (25 mg), THF (5 mL), stearyl methacrylate (1.0 g), and N-(polyoxaperfluoroacyl)-2-aminoethyl methacrylate (2.0 g). The mixture was heated to 60° C. for 15 h. The reaction mixture became very viscous and was poured into MeOH (50 mL). The precipitated polymer was washed with MeOH (2×20 mL) and dried under vacuum to give a solid (2.5 g). It was a copolymer and contained about 23.5% F by NMR.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Example 11

A mixture of ethanolamine (13 g, 28 mmole) and ether (30 mL) was cooled to 15° C. Perfluoro-2-methyl-3-oxahexanoyl fluoride (33 g in ether 50 mL) was added dropwise to keep the reaction temperature below 25° C. After the addition, the reaction mixture was stirred at room temperature for one hour. The solid was removed by filtration and the filtrate was washed with hydrochloric acid (0.5N, 30 mL), water (2 times 30 mL), sodium hydrogen carbonate solution (0.5N, 20 mL), water (30 mL), and sodium chloride solution (saturated, 20 mL). It was then concentrated and dried in vacuum over night at room temperature to give a white solid 35 g, yield 95%. H NMR ($CDCl_3$) 1.67 (br s, 1H), 3.57 (m, 2H), 3.80 (t, J=5 Hz, 2H), 6.91 (br s, 1H) ppm. F NMR ($CDCl_3$) −81.2 (dm, J=148 Hz, 1F), −81.7 (t, J=7 Hz, 3F), −82.7 (d, J=3 Hz, 3F), −85.2 (dm, J=148 Hz, 1F), −130.1 (s, 2F), −133.2 (m, 1F) ppm. The product is N-(perfluoro-2-methyl-3-oxahexanoyl)-2-aminoethanol.

A 250-mL flask was charged with triethylamine (8.2 g), THF (80 mL), and N-(perfluoro-2-methyl-3-oxo-hexanoyl)-2-aminoethanol (25 g). Methacryloyl chloride (8.44 g in tetrahydrofuran, 20 mL) was added dropwise to the above mixture at 5° C. The mixture was stirred at room temperature overnight. The reaction mixture was poured into water (200 mL) and two layers were formed. The aqueous layer (top layer) was extracted with methylene chloride (five time 50 mL). The combined methylene chloride extracts and original organic layer were washed with water (six times 60 mL), neutralized with dilute hydrochloric acid (0.5N), dried over anhydrous sodium sulfate, concentrated and dried on vacuum to give a oil, N-(perfluoro-2-methyl-3-oxahexanoyl)-2-aminoethyl methacrylate (27.06 g), yield 92%. H NMR ($CDCl_3$) 1.94 (m, 3H), 3.72 (m, 2H), 4.33 (m, 2H), 5.63 (m, 1H), 6.12 (m, 1H), 6.88 (br s, 1H) ppm. F NMR ($CDCl_3$) −81.2 (dm, J=148 Hz, 1F), −81.7 (t, J=7 Hz, 3F), −82.7 (d, J=3 Hz, 3F), −85.2 (dm, J=148 Hz, 1F), −130.1 (s, 2F), −133.4 (m, 1F) ppm.

In a dry box, a mixture of VAZO 52 (47 mg), THF (5 mL), stearyl methacrylate (1.91 g), and N-(perfluoro-2-methyl-3-oxahexanoyl)-2-aminoethyl methacrylate (2.48 g) was heated to 60° C. for 17 hours. The reaction mixture was poured into methanol (60 mL) and the precipitated polymer was washed with methanol and dried on vacuum to give a solid 3.72 g. It was a copolymer of N-(perfluoro-2-methyl-3-oxahexanoyl)-2-aminoethyl methacrylate and stearyl methacrylate and contained 22% F. A solution of the copolymer was prepared and was applied to cotton and nylon fabric using the procedure of Test Method 1. The treated fabric was tested for water repellency and oil repellency using Test Methods 2 and 3, respectively. The results are in Table 3.

Comparative Example A

Under a nitrogen atmosphere charged a 20 mL vial with 1H,1H,2H,2H-perfluorooctylacrylate (2.0 g), obtained from SynQuest Fluorochemicals (Alachua, Fla.), stearyl methacrylate (1.2 g), tetrahydrofuran (8 mL), and 2,2'-azobis(2,4-dimethylpentanenitrile) (23 mg). The reaction was heated at 60° C. for 21 h. After being cooled to room temperature, the reaction mixture was poured into methanol (100 mL). The precipitated polymer was washed with methanol (20 mL) and dried under vacuum to give polymer (2.56 g).

A solution of the copolymer was prepared and was applied to cotton and nylon fabric using the procedure of Test Method 1. The treated fabric was tested for water repellency and oil repellency using Test Methods 2 and 3, respectively. The results are in Table 3.

Comparative Example B

A 250-mL flask was charged with 1H,1H,2H,2H-perfluorodecyl acrylate obtained from SynQuest Fluorochemicals (Alachua, Fla.) (20.4 g), stearyl methacrylate (13.5 g), 1-dodecanethiol (0.2 g), 2,2'-azobis(2-methylbutyronitrile, (VAZO 67, 0.4 g), and tetrahydrofuran (100 mL). The flask was cooled to 18° C. and flushed with nitrogen for 30 min. The reaction mixture was heated for 14.5 h at 66° C. using a 75° C. oil bath. A reaction mixture (115.4 g) was obtained. Its solid content was determined by the following procedure: a sample (1.82 g) of the reaction solution was dried under vacuum at 80° C. to give a solid, 0.56 g.

A solution of the copolymer was prepared and was applied to cotton and nylon fabric using the procedure of Test Method 1. The treated fabric was tested for water repellency and oil repellency using Test Methods 2 and 3, respectively. The results are in Table 3.

TABLE 3

|  | On Cotton | | On Nylon | |
|---|---|---|---|---|
| Example | Oil Repellency | Water Repellency | Oil Repellency | Water Repellency |
| 1 | 2 | 4 | 5 | 7 |
| 2 | 0 | 3 | 5 | 5 |
| 3 | 1 | 3 | 2 | 7 |
| 4 | 2 | 2 | 6 | 5 |
| 5 | 4 | 7 | 5 | 7 |
| 6 | 0 | 4 | 2 | 7 |
| 7 | 3 | 4 | 5 | 7 |
| 8 | 3 | 7 | 5 | 9 |
| 9 | 2 | 5 | 4 | 7 |
| 10 | 2 | 6 | 2 | 6 |
| 11 | 1 | 5 | 3 | 7 |
| Comparative A | 0 | 0 | 0 | 4 |
| Comparative B | 0 | 4 | 0 | 7 |

The data in Table 3 demonstrated the Examples are comparable or better than the prior art. For cotton, Examples 3 and 4 had a perfluoroalkyl chain length of 4 carbons, so this represents the lower limit for water repellency but provided superior oil repellency. For nylon, Comparative Example B had 8 carbons in the perfluoroalkyl chain, and for water repellency the Examples of the present invention having 4 or 6 carbons were comparable. For nylon, the Examples of the present invention were superior for oil repellency.

What is claimed is:

1. A composition comprising Formula 2

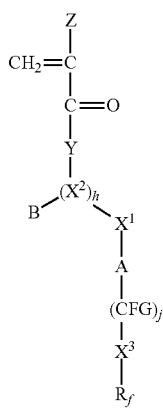

Formula 2 wherein
$R_f$ is a linear perfluoroalkyl group having from about 1 to about 20 carbon atoms, or a mixture thereof, which is optionally interrupted by at least one oxygen atom,
$X^3$ is oxygen or $X^1$,
each $X^1$ is independently an organic divalent linking group having from about 1 to about 20 carbon atoms, optionally containing an oxygen, nitrogen, or sulfur, or a combination thereof,
G is F or $CF_3$,
A is an amide,
j is zero or positive integer, provided that when Y is N, j is a positive integer,
$X^2$ is an organic linking group,
Y is O, N or S,
h is zero when Y is N, and h is one when Y is O or S,
Z is H, a straight or branched alkyl group having from about 1 to about 4 carbon atoms, or halide, and
B is H or

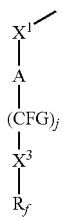

wherein
$R_f$, $X^1$, $X^3$, G, A, and j are as defined above.

2. A composition comprising Formula 3

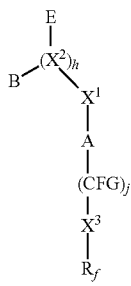

wherein $R_f$ is a linear perfluoroalkyl group having from about 1 to about 20 carbon atoms, or a mixture thereof, which is optionally interrupted by at least one oxygen atom, $X^3$ is oxygen or $X^1$, each $X^1$ is independently an organic divalent linking group having from about 1 to about 20 carbon atoms, optionally containing an oxygen, nitrogen, or sulfur, or a combination thereof, G is F or $CF_3$, A is an amide, j is a positive integer, $X^2$ is an organic linking group, h is zero or one

and B is H or wherein $R_f$, $X^1$, $X^3$, G, A, and j are as defined above, and E is selected from the group consisting of hydroxyl, amine, halogen and thiol, provided that h is zero when E is amine, and h is one when E is other than amine.

3. The composition of claim 1 or 2 wherein $R_f$ is a perfluoroalkyl group having the formula $F(CF_2CF_2)_n$, wherein n is 2 to about 20, or mixtures thereof.

4. The composition of claim 3 wherein n is 3 or 6.

5. The composition of claim 1 or 2 wherein $X^1$ is selected from the group consisting of a straight chain, branched chain or cyclic alkylene, phenyl, arylene, aralkylene, sulfonyl, sulfoxy, sulfonamido, carbonamido, carbonyloxy, urethanylene, ureylene, and combinations thereof.

6. The composition of claim 1 or 2 wherein $X^2$ is $R^5C$ wherein $R^5$ is H or $C_1$ to $C_4$ alkyl.

* * * * *